United States Patent [19]
Sikkenga

[11] Patent Number: 4,891,467
[45] Date of Patent: Jan. 2, 1990

[54] SELECTIVE SYNTHESIS OF PSEUDOCUMENE AND DURENE

[75] Inventor: David L. Sikkenga, Wheaton, Ill.

[73] Assignee: Amoco Corporation, Chicago, Ill.

[21] Appl. No.: 776,221

[22] Filed: Sep. 16, 1985

Related U.S. Application Data

[63] Continuation of Ser. No. 660,918, Oct. 15, 1984, abandoned, which is a continuation of Ser. No. 507,058, Jun. 23, 1983, abandoned.

[51] Int. Cl.$^4$ .................................................. C07C 2/68
[52] U.S. Cl. ..................................................... 585/467
[58] Field of Search ........................................ 585/467

[56] References Cited
U.S. PATENT DOCUMENTS
4,292,457 9/1981 Klotz .................................. 585/467

OTHER PUBLICATIONS

A copy of the reference was provided in your parent application Ser. No. 06/507,058.

Primary Examiner—Curtis R. Davis
Attorney, Agent, or Firm—Wallace Oliver; William H. Magidson; Ralph C. Medhurst

[57] ABSTRACT

A catalytic process is provided for the selective production of pseudocumene and durene by contacting a hydrocarbon feed containing benzene or a methyl substituted benzene under methylating conditions and in the presence of a methylating agent with a catalyst comprising AMS-1B crystalline borosilicate. In the resulting product pseudocumene and durene are obtained in selectivities higher than equilibrium concentrations of respectively trimethylbenzenes and tetramethylbenzenes.

25 Claims, No Drawings

SELECTIVE SYNTHESIS OF PSEUDOCUMENE AND DURENE

This is a continuation of application Ser. No. 660,918, filed Oct. 15, 1984 which is a continuation of No. 507,058 filed June 23, 1983, both now abandoned.

BACKGROUND OF THE INVENTION

This invention relates to a catalytic process for the selective synthesis of pseudocumene and durene by methylation of benzene or methyl substituted benzenes using a particular crystalline borosilicate type of molecular sieve. In the resulting product pseudocumene and durene are substantially in excess of equilibrium concentrations among trimethylbenzenes and tetra-methylbenzenes respectively.

There is increasing recognition that petroleum is not a replenishable resource, and that its availability and cost are subject to unpredictable change. It is desirable to seek alternative processes that convert nonpetroleum raw materials to hydrocarbons useful as petrochemicals. The present invention, which utilizes alcohol as raw material, is such a process. Alcohols can be prepared from agricultural products, or from coal, or from petroleum by-products, or from natural gas.

Several polymethylbenzenes are important intermediate products in the chemical industry. Particular di-, tri-, and tetra-methylbenzenes are oxidized to produce polycarboxylic acids and anhydrides of aromatic acids which are useful in the manufacture of synthetic fibers and plastics. Recent interest in manufacturing anhydrides of the most important aromatic tri-, and tetracarboxylic acids, trimellitic (1,2,4-benzene-tricarboxylic acid) and pyromellitic (1,2,4,5-benzene-tetacarboxylic acid), is due to their use, respectively, in trimellitic ester plasticizers and polyimide resins. The commercial method of producing trimellitic and pyromellitic anhydrides is by oxidation of the corresponding tri- and tetramethylbenzenes, pseudocumene (1,2,4-trimethylbenzene) and durene (1,2,4,5-tetramethylbenzene). These aromatic hydrocarbons, which as purified raw materials constitute the largest single items of cost in the manufacture of the anhydrides, are recovered by super fractionation and crystallization. Such processes, as will be realized, have involved high operation costs and have limited yields.

Fractionation of a mixed aromatics stream such as an extracted, heavy catalytic reformate is suitable to recover purified pseudocumene provided non-aromatics are absent. The close fractionation necessary is done in two fractionators (each containing about 100 trays) which remove, successively, aromatics boiling above and below pseudocumene. Typically the fractionation feed of $C_9$ aromatics from hydroformates contain only about 40 percent pseudocumene. Such low pseudocumene content requires relatively large fractionation towers.

While durene, because of its high freezing point (about 79° C.), could be recovered in pure form by crystallization from a concentrate distilled from $C_{10}$ reformate aromatics, the low durene content of such concentrate (about 19 percent) makes this impractical. Durene recovery by a crystallization process is made difficult by the high viscosity of the mother liquor at low temperatures, by the small size of the crystals and by the plate crystal structure which tends to trap liquid and prevent a clean separation of mother liquor from crystals. The crystallization process is easier at higher concentration of durene. Accordingly, methods such as methylating pseudocumene which obtain a durene content in the tetramethylbenzene mixture of about ½ may be useful to provide a feed for the crystallization step to recover durene in pure form. The principal problem has been to develop catalysts and reaction conditions to give good yields while avoiding excessive coke formation and catalyst deactivation.

Synthesis of durene by condensation of 1,2,4-trimethylbenzene and methanol over silver-silica-alumina catalyst has been described by Kobayashi et al. in Sekiya Gakkai Shi 13 (10), 775–80 (1970). These workers reported pseudocumene conversion of 33.7 percent and the selectivities for durene and tetramethylbenzenes of 33.8 and 61.8 percent, respectively, under the optimal conditions of 250° C., 2.0 liquid hourly space velocity, 2:1 molar ratio of hydrogen to pseudocumene plus methanol, and 2:1 molar ratio pseudocumene to methanol. The conversion decreased when hydrogen was not used as diluent.

Methylation of pseudocumene using methanol containing less than 1 mole percent $(MeO)_3B$ as a methylating agent in the presence of $SiO_2$-$Al_2O_3$-AgO catalyst is described in Japan, Kokai 74 43,930 to Nakano. A mixture of pseudocumene, methanol, and $(MeO)_3B$ was passed at 250° C. and 1 hr.$^{-1}$ liquid hourly space velocity through a packed catalyst to give a product mixture in which the tetramethylbenzenes were about one-half durene.

Production of durene by toluene methylation using methyl chloride as methylating agent in the presence of aluminum chloride is described by Plyusnin et al. in Tr. Inst. Khim., Ural. Nauchn. Tsentr. Akad. Nauk SSSR 2G, 40-7 (1974). These workers report up to 52.0 percent durene content in the tetramethylbenzenes obtained at 120° C. for 11 hours.

Alkylation of aromatic hydrocarbons utilizing boria containing catalysts has heretofore been described. U.S. Pat. No. 3,217,053 to Kovach et al. claims alkylation of aromatic hydrocarbons with an alcohol or an ether in the presence of a catalyst consisting of a major amount of a calcined alumina base and minor amounts of phosphorus pentoxide and boria, respectively about 0.1 to 20 weight percent and about 0.1 to 10 weight percent. U.S. Pat. No. 3,230,270 to Kovach et al. describes alkylation of aromatic hydrocarbons with methanol in the presence of a catalyst consisting of a calcined alumina base and minor amounts of chromic sesquioxide and boria. The boria is claimed to enhance the utilization of the alkylating agent when said boria is dispersed on the surface of the precalcined gamma-alumina support in direct proportion to the area of the support. Products were reported from $C_8$ to $C_{12}$ without identification of individual isomers.

Various processes for conversion of aromatic compounds are known to employ particular crystalline aluminosilicate zeolite catalysts mixed with a boron-containing additive, such as the disproportionation of toluene described in U.S. Pat. No. 4,029,716. The production of styrene and ethylbenzene by reacting toluene and methanol with a catalyst having an aluminosilicate zeolite of the faujasite structure with potassium, rubidium or cesium cations and containing impregnated boron or phosphorus compounds is described in U.S. Pat. No. 4,140,726.

Although the above background is considered of interest in connection with the subject matter of the present invention, the methylation process described herein uses a catalyst comprising an AMS-1B crystalline borosilicate molecular sieve to achieve unexpectedly high selective production of pseudocumene and durene.

Compared to a conventional thermodynamic equilibrium trimethylbenzene mixture in which the 1,2,4-:1,3,5-: 1,2,3-ratio is approximately 17:6:2, the present invention provides a trimethylbenzene product in which the 1,2,4-trimethylbenzene content may exceed 85 percent. This improved selectivity to pseudocumene reduces the cost of separation of 1,2,4-trimethylbenzene from its isomers which is the most expensive step in the current method employed for the production of pseudocumene.

Further, the methylation process described herein provides a tetramethylbenzene product in which durene content may exceed 95 percent in contrast to a typical thermodynamic equilibrium tetramethylbenzene mixture in which the isodurene:durene:prehnitene ratio is about 5:3:2. The high selectivities to pseudocumene and durene of this invention affords yield and cost advantages to the separation steps to produce these isomers in pure forms.

SUMMARY OF THE INVENTION

Pseudocumene (1,2,4-trimethylbenzene) and durene (1,2,4,5-tetramethylbenzene) can be produced selectively by contacting a hydrocarbon feed comprising benzene or a methyl-substituted benzene under methylating conditions in the presence of a methylating agent with a catalyst comprising AMS-1B crystalline borosilicate.

BRIEF DESCRIPTION OF THE INVENTION

This invention is a method to convert an aromatic hydrocarbon feed, especially a feed containing monocyclic aromatic hydrocarbons to trimethylbenzenese and tetramethylbenzenes. More particularly, this invention is a catalytic process using an ASM-1B crystalline borosilicate-based catalyst system for methylation of benzene or an alkyl-substituted benzene to produce a mixture containing pseudocumene and durene at concentrations higher than equilibrium concentrations among trimethylbenzenes and tetramethylbenzenes respectively.

Aromatic hydrocarbons have chemical structures related to benzene, i.e., a molecule consisting of six carbon atoms in a ring with one hydrogen on each carbon. A natural source of aromatic compounds is coal tar. As one division in the classification of organic substances aromatic hydrocarbons include monocyclic compounds, e.g., benzene, toluene and isomers of xylene, and compounds having fused benzene rings, e.g., naphthalene which contains two fused rings or anthracene and phenanthrene which contain three fused benzene rings.

Hydrocarbons which can be converted using the process of this invention include monocyclic aromatic hydrocarbons containing up to about 12 carbon atoms such as benzene, toluene, and alkyl-substituted benzenes. The preferable feed useful in this invention comprises benzene and methyl substituted benzenes such as toluene, xylenes, trimethylbenzenes and tetramethylbenzenes. Mixtures of monocyclic aromatic hydrocarbons can be used in the process of this invention.

The monocyclic aromatic hydrocarbons, or mixtures thereof, used in the process of this invention can be converted in the presence of other substances such as other hydrocarbon-based molecules. Thus, a feed used in the process of this invention comprising a monocyclic aromatic hydrocarbon also can contain other hydrocarbons such as alkanes, alkenes, methane, hydrogen, and inert gases. A process in which partially reacted hydrocarbons are recycled will contain a mixture including alkanes, alkenes, methane and aromatics. Typically a monocyclic aromatic hydrocarbon feed used in this invention contains about 10 to 100 wt.% monocyclic aromatic hydrocarbon and preferably contains about 50 to 100 wt.% monocyclic aromatic hydrocarbon.

Methanol is typically the methylating agent, but also useful in the present invention are other known methylating agents, including, methyl chloride, methyl bromide, dimethylether or dimethylsulfide and the like.

The catalyst useful in this invention is based on the crystalline borosilicate molecular sieve, ASM-1B, described in U.S. Pat. Nos. 4,268,420, 4,269,813, and 4,285,919 incorporated herein by reference. A particularly useful catalyst for this invention contains AMS-1B in which a metal is placed by ion exchange, impregnation or other means.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9 \pm 0.2 M_{2/n}O : B_2O_3 : ySiO_2 : zH_2O$$

wherein M is at least one cation, n is the valence of the cation, y is between 4 and about 600 and z is between 0 and about 160.

TABLE 1

| d-Spacing Å (1) | Assigned Strength (2) |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

The AMS-1-B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
| --- | --- | --- | --- |
| SiO$_2$/B$_2$O$_3$ | 5-400 | 10-150 | 10-80 |
| R$_2$O$^+$/[R$_2$O$^+$ + M$_{2/n}$O] | 0.1-1.0 | 0.2-0.97 | 0.3-0.97 |
| OH$^-$/SiO$_2$ | 0.01-11 | 0.1-2 | 0.1-1 |
| H$_2$O/OH$^-$ | 10-4000 | 10-500 | 10-500 | wherein R is an organic compound and M is at least one cation having a valence n, such as an alkali metal or an alkaline earth metal cation. By regulation of the quantity of boron (represented as $B_3O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraallkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0\pm0.2$ using a compatible acid or base such as sodium bisulfate or sodium hydroxide. After sufficient quantities of silicic acid polymer (Ludox) are added with intensive mixing, preferably the pH is again checked and adjusted to a range of about $11.0\pm0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 250° to about 850° C. and preferably about 425° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Catalyst compositions useful in this invention preferably contain hydrogen-form AMS-1B crystalline borosilicate molecular sieve.

In addition, preferable catalyst compositions are prepared containing Group VIII elements while most preferable Group VIII elements having atomic number below 46. Such catalytically active non-nobel metals include ruthenium, rhodium, iron, cobalt, and nickel; cobalt and nickel are preferable while nickel is the most preferable. Mixtures of Group VIII elements can be used.

Furthermore, preferable catalyst compositions are prepared containing a non-nobel metal of Group VIII in combination with another metal ion or compound including Groups IB, IIB, IIIB, IVB, VB, VIB, VIIB and VIII metals and rare earth elements. Specific additional catalytic materials include ions and compounds of lanthanum, molybdenum, tungsten, and noble metals. Such noble metals include ruthenium, osmium, rodium, iridium, palladium, and platinum. Other additional catalytic materials can be ions and compounds of scandium, yttrium, titanium, zirconium, hafnium, vanadium, niobium, tantalum, chromium, cerium, manganese, iron, zinc and cadmium. Specific combinations of non-noble metals of Group VIII and other catalytic materials include ions or compounds of nickel and osmuim, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention may be used as pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt.% if the total composition. Catalytic compositions can contain about 0.1 wt.% to about 100 wt.% crystalline borosilicate material and preferably contain about 10 wt.% to about 95 wt.% of such material and most preferably contain about 20 wt.% to about 80 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813 and European Published Application No. 68,796 both incorporated by reference herein.

In a process using this invention, a feedstream containing a monocyclic aromatic hydrocarbon, such as toluene, is contacted with a methylating agent and a catalytic material containing AMS-1B borosilicate. Catalyst may be in a fixed or fluidized bed. In the preferable process of this invention a methyl-substituted benzene is contacted with the above-described AMS-1B borosilicate-based catalyst system in the liquid or vapor phase at a suitable reaction temperature, pressure and space velocity. Generally, suitable reaction conditions include a temperature between about 200° F. (93° C.) and about 1,100° F. (593° C.) and preferably about 400° F. (204° C.) and about 1,000° F. (538° C.) The catalytic conversion generally takes place at any convenient pressure within the approximate range of about 1 atmosphere (0 psig) to 2,000 psig (preferably in the range 0 to 1,000 psig). Advantageously, to minimize catalyst coking, a diluent gas such as hydrogen is used at a free hydrogen-to-hydrocarbon mole ratio of about 0.05 to about 20. When methanol is employed as the methylating agent a suitable molar ratio of methanol to hydrocarbon has been found to be between about 0.05 and about 20. Conversion is suitable accomplished at weight hourly space velocity (WHSV) of about 0.01 weight unit of feed per hour per weight unit of catalyst (hr.$^{-1}$) to about 90 hr.$^{-1}$. The reactor effluent consisting predominantly of monocyclic methyl-substituted aromatic hydrocarbons may be separated by any suitable means, such as close fractionation and crystallization.

Generally the methylating agent is methanol, but also useful in the present invention are other known methylating agents, including, methyl chloride, methyl bromide, dimethylether or dimethylsulfide.

Operating conditions for conversion of a feed comprising toluene broadly comprise a temperature of about 200° F. (93° C.) to about 1,000° F. (538° C.), a free hydrogen-to-hydrocarbon mole ratio of about 0.05 to about 20, a methylating agent-to-hydrocarbon mole ratio of about 0.05 to about 20, weight hourly space velocity (WHSV) or about 0.01 weight unit of feed per hour per weight unit of catalyst (hr.$^{-1}$) to about 90 hr.$^{-1}$, and a pressure of ambient, i.e., 0 psig to about 2,000 psig. Advantageously, the conditions comprise a temperature of about 400° F. (204° C.) to about 950° F. (510° C.), a free hydrogen-to-hydrocarbon mole ratio of about 0.1 to about 18, a methylating agent-to-hydrocarbon mole ratio of about 0.1 to about 20, a WHSV of about 0.1 hr.$^{-1}$ to about 50 hr.$^{-1}$ and a pressure in the range of 0 psig to about 1500 psig.

Preferred conditions for the conversion of toluene comprise a temperature of about 500° F. (260° C.) to about 900° F. (482° C.), a free hydrogen-to-toluene mole ratio of about 1 to about 12, a methanol-to-toluene mole ratio of about 0.1 to about 16, a WHSV of about 0.5 hr.$^{-1}$ to about 50 hr.$^{-1}$, and a pressure of about 0 psig to about 1,000 psig.

Operating conditions for conversion of a feedstream comprising xylenes comprise a temperature of about 260° F. (127° C.) to about 1,000° F. (538° C.), a free hydrogen-to-hydrocarbon mole ratio of about 0.05 to about 20, a methylating agent-to-hydrocarbon mole ratio of about 0.05 to about 20, a weight hourly space velocity (WHSV) of about 0.01 weight unit of feed per hour per weight unit of catalyst (hr.$^{-1}$) to about 90 hr.$^{-1}$, and a pressure of ambient, i.e., 0 psig to about 2,000 psig. Advantageously, the conditions comprise a temperature of about 460° F. (237° C.) to about 950° F. (510° C.), a free hydrogen-to-hydrocarbon mole ratio of about 0.1 to about 18, a methylating agent-to-hydrocarbon mole ratio of about 0.1 to about 20, a WHSV of about 0.05 to about 45 hr.$^{-1}$ and a pressure in the range of 0 psig to about 1,500 psig.

Preferred conditions for the conversion of xylenes comprise a temperature of about 540° F. (282° C.), to about 900° F. (482° C.), a free hydrogen-to-$C_8$ aromatic mole ratio of about 1 to about 12, a methanol-to-$C_8$ aromatic mole ratio of about 0.1 to about 16, a WHSV of about 0.1 hr.$^{-1}$ to about 45 hr.$^{-1}$, and a pressure of about 0 psig to about 1,000 psig.

In another embodiment of the invention durene is selectively synthesized by catalytic conversion of a feed comprising pseudocumene in the presence of a methylating agent. Operating conditions for the conversion of feed comprising pseudocumene comprise a temperature of about 300° F. (149° C.), to about 1,000° F. (538° C.), a free hydrogen-to-hydrocarbon mole ratio of about 0.05 to about 20, a methylating agent-to-hydrocarbon mole ratio of about 0.05 to about 20, weight hourly space velocity (WHSV) of about 0.01 weight unit of feed per hour per weight unit of catalyst (hr.$^{-1}$) to about 90 hr.$^{-1}$, and a pressure of ambient, i.e., 0 psig to about 2,000 psig. Advantageously, the conditions comprise a temperature of about 460° F. (237° C.) to about 950° F. (510° C.), a free hydrogen-to-hydrocarbon mole ratio of about 0.1 to about 12, a methylating agent-to-hydrocarbon mole ratio of about 0.1 to about 20, a WHSV of about 0.05 to about 40 hr.$^{-1}$ and a pressure in the range of 0 psig to about 1,5000 psig.

Preferred conditions for the conversion of pseudocumene comprise a temperature of about 560° F. (293° C.), to about 900° F. (482° C.), a free hydrogen-to-pseudocumene mole ratio of about 1 to about 12, a methanol-to-pseudocumene mole ratio of about 0.1 to about 15, a WHSV of about 0.1 hr.$^{-1}$ to about 35 hr.$^{-1}$, and a pressure of about 0 psig to about 1,000 psig.

The process of this invention converts benzene and methyl-substituted benzene to pseudocumene and durene with good selectivities. Typically, 65 to 85 percent and more of product trimethylbenzenes is 1,2,4-trimethylbenzene and 50 to 95 percent and more of product tetramethylbenzenes is 1,2,4,5-tetramethylbenzene. These high selectivities to pseudocumene and durene afford yield and cost advantages to separation steps to produce pseudocumene and durene in pure forms.

The following examples illustrate certain specific embodiments of the invention, but do not limit the scope of the invention. As those of skill in the art will recognize, there are many variations which may be made within the spirit of the disclosed invention.

EXAMPLE I

In this example, AMS-1B crystalline borosilicate prepared according U.S. Pat. Nos. 4,268,420 and 4,269,813 which contained 0.72 wt.% boron was used to prepare a catalyst having methylation capabilities.

The AMS-1B material was calcined at 1000° F. (538° C.) in air for 4 hours to remove the organic base. A quantity of 20 gm of the calcined sieve was exchanged one time with a solution of 200 gm. $NH_4NO_3$ in 2 l of $H_2O$ at 185° F. (85° C.) for 2 hours and then a second time with 200 gm of ammonium acetate in 2 l of $H_2O$. The exchanged borosilicate was dried and calcined in air by heating it to 1,000° F. (538° C.) in 4 hours, maintaining the borosilicate at 1,000° F. (538° C.) for 4 hours, and then cooling to 100° F. (38° C.) for 4 hours, and then cooling to 100° F. (38° C.) in 4 hours. The above ammonium exchange procedure was then repeated on an additional 240 gm of sieve, however only ammonium acetate used. A quantity of 200 gm of calcined material was exchanged with 10 l of 5 percent $Ni(NO_3)_2 \cdot 6H_2O$ solution for 2 hours at 185° F. (85° C.). The sieve was washed with $H_2O$ and the excess $Ni^{+1}$ ions were washed out of the sieve. The sieve was dried and calcined again using the above procedure. About 200 gm of the borosilicate were dispersed in 200 gm of PA-$Al_2O_3$ powder (obtained from American Cyanamid Co.) and a small quantity of $H_2O$. Extrudates made from this mixture were dried and activated by a fourth programmed calcination. The calcined catalyst contained 50 wt.% borosilicate and 50 wt.% amorphous alumina with approximately 320 ppm of the total solid as nickel.

Ten grams of the extruded and activated catalyst was placed in a ½ inch tubular stainless steel reactor and heated to 800° F. (427° C.) under $H_2$ pressure of about 200 psig. The catalyst was reduced for 2 hours before hydrocarbon feed was started. Methanol and toluene in a molar ratio mixture of 1.0 were passed through the tubular reactor under the following once-through conditions

| | |
|---|---|
| Temperature | 800° F. (427° C.) |
| Pressure | 197 psig |
| WHSV | 8.3 |
| H/HC, mole ratio | 6.7 |

The reactor effluent stream was sampled for analysis after cooling to ambient temperature and reducing pressure to about 3 psig.

The liquid hydrocarbon composition of the reactor effluent stream for this operation is shown below. Because of the equipment limitation on the screening unit, only analyses on liquid streams were obtained and reported. The light-end production over this catalyst was low from the gas chromatographic analysis made on the off-gas stream from the unit. The volume of off-gas was determined to not substantially reduce overall liquid yields over the catalyst.

Reactor Effluent

| Reactor Effluent Liquid Hydrocarbon Composition (Wt. %) | |
|---|---|
| Paraffin and Naphthenes | 0.35 |
| Toluene | 39.8 |
| $C_8$ Aromatics | 39.9 |

-continued

| Reactor Effluent | |
|---|---|
| Liquid Hydrocarbon Composition (Wt. %) | |
| Methylethylbenzenes | 1.7 |
| 1,3,5-Trimethylbenzene | 0.31 |
| 1,2,4-Trimethylbenzene | 14.1 |
| 1,2,3-Trimethylbenzene | 0.31 |
| Dimethylethylbenzenes | 0.45 |
| Diethylbenzenes | 0.32 |
| 1,2,3,5-Tetramethylbenzenes | 0.40 |
| 1,2,4,5-Tetramethylbenzenes | 2.80 |
| 1,2,3,4-Tetramethylbenzenes | 0.16 |
| Other | 0.09 |

These data show the catalyst has methylation capabilities including high capabilities including high selectivity to pseudocumene and durene. The trimethylbenzenes produced contained 96 percent 1,2,4-trimethylbenzene and the tetramethylbenzenes contained 83 percent 1,2,3,4,5-Tetramethyl-benzene.

EXAMPLES II–VI

Methanol and toluene in molar ratio mixture of 2 and 3 were passed over the catalyst from Example I with varying hydrogen to toluene mole ratio. The conditions and results are shown below.

| EXAMPLE | II | III | IV | V | VI |
|---|---|---|---|---|---|
| Feed Composition, Mole Ratio | | | | | |
| Methanol/Toluene | 2.0 | 2.0 | 2.0 | 2.0 | 3.0 |
| H/HC | 6.6 | 5.8 | 5.3 | 4.2 | 7.8 |
| Reactor Conditions | | | | | |
| Temperature (°F.) | 587 | 692 | 797 | 901 | 584 |
| Pressure (psig) | 197 | 197 | 197 | 197 | 197 |
| LWHSV (g liquid/hr) (g cat.) | 8.8 | 8.8 | 8.8 | 8.7 | 8.6 |
| Contact Time (Sec.) | 4.1 | 4.1 | 4.0 | 4.3 | 4.1 |
| Days on Stream | 28 | 29 | 30 | 31 | 33 |
| Liquid Hydrocarbon Composition (Wt. %) | | | | | |
| Paraffin and Naphthenes | 1.76 | 2.59 | 2.12 | 1.65 | 2.38 |
| Toluene | 53.2 | 35.4 | 30.1 | 33.0 | 64.4 |
| $C_8$ Aromatics | 28.3 | 33.4 | 39.4 | 41.1 | 22.3 |
| Methylethylbenzenes | 0.5 | 3.03 | 3.18 | 3.77 | 0.31 |
| 1,3,5-Trimethylbenzene | 0.0 | 0.04 | 0.20 | 0.31 | 0.0 |
| 1,2,4-Trimethylbenzene | 9.05 | 15.5 | 17.9 | 15.7 | 6.23 |
| 1,2,3-Trimethylbenzene | 0.78 | 0.28 | 0.19 | 0.19 | 0.51 |
| Dimethylethylbenzenes | 0.18 | 1.00 | 0.79 | 0.67 | 0.11 |
| Diethylbenzenes | 0.12 | 0.67 | 0.46 | 0.36 | 0.0 |
| 1,2,3,5-Tetramethylbenzenes | 0.0 | 0.22 | 0.40 | 0.32 | 0.0 |
| 1,2,4,5-Tetramethylbenzenes | 5.50 | 7.31 | 4.70 | 2.31 | 3.66 |
| 1,2,4,5-Tetramethylbenzenes | 0.0 | 0.07 | 0.11 | 0.08 | 0.0 |
| Other | 0.63 | 0.58 | 0.44 | 0.61 | 0.31 |
| Selectivity, Percent | | | | | |
| Pseudocumene in Total Trimethylbenzenes | 92 | 98 | 98 | 97 | 92 |
| Durene in Total Tetramethylbenzenes | 100 | 96 | 90 | 85 | 100 |

EXAMPLES VII–IX

Methanol and ortho-xylene in molar ratio mixture of 2 were passed over the catalyst from Example I with varying hydrogen to ortho-xylene mole ratio. The conditions and results are shown below.

| EXAMPLE | VII | VIII | IX |
|---|---|---|---|
| Feed Composition, Mole Ratio | | | |
| Methanol/Xylene | 2 | 2 | 2 |
| H/HC | 7.3 | 5.8 | 4.9 |
| Reactor Conditions | | | |
| Temperature (°F.) | 626 | 740 | 844 |
| Pressure (psig) | 198 | 198 | 198 |
| LWHSV (g liquid/hr) (g cat.) | 6.7 | 6.7 | 6.7 |
| Contact Time (Sec.) | 5.7 | 6.1 | 6.3 |
| Days on Stream | 1.8 | 4.8 | 6.2 |
| Liquid Hydrocarbon Composition (Wt. %) | | | |
| Paraffin and Naphthenes | 0.75 | 3.36 | 3.94 |
| Toluene | 1.16 | 0.54 | 0.73 |
| $C_8$ Aromatics | 81.8 | 61.0 | 57.5 |
| Methylethylbenzenes | 0.17 | 0.17 | 0.52 |
| 1,3,5-Trimethylbenzene | 0.0 | 0.0 | 0.10 |
| 1,2,4-Trimethylbenzene | 10.6 | 20.89 | 25.07 |
| 1,2,3-Trimethylbenzene | 0.23 | 0.69 | 2.67 |
| Dimethylethylbenzenes | 0.08 | 2.99 | 1.21 |
| Diethylbenzenes | 0.0 | 0.0 | 0.0 |
| 1,2,3,5-Tetramethylbenzenes | 0.0 | 0.27 | 0.58 |
| 1,2,4,5-Tetramethylbenzenes | 4.38 | 8.66 | 6.72 |
| 1,2,3,4-Tetramethylbenzenes | 0.02 | 0.08 | 0.45 |
| Other | 0.81 | 0.75 | 0.51 |
| Selectivity, Percent | | | |
| Pseudocumene in Total Trimethylbenzenes | 98 | 97 | 90 |
| Durene in Total Tetramethylbenzenes | 99.5 | 96 | 87 |

EXAMPLE X

Another catalyst extrudate was prepared similarly to the method described in Example I using AMS-1B crystalline borosilicate which contained 0.74 wt.% boron. The calcined catalyst contained approximately 498 ppm of the total solid as nickel.

After the extruded catalyst was reduced as described in Example I, methanol and meta-xylene in a molar ratio mixture of 2 were passed over the catalyst along with hydrogen in mole ratio H/HC of 4.9 at reactor conditions

| Temperature | 690° F. (366° C.) |
|---|---|
| Pressure | 198 psig |
| WHSV | 6.7 |

The reactor effluent was cooled to ambient temperature and pressure reduced to about 3 psig for sampling and analysis. The results are given below.

Reactor Effluent

| Reactor Effluent | |
|---|---|
| Liquid Hydrocarbon Composition Wt. % | |
| Paraffin and Naphthenes | 5.35 |
| Toluene | 0.33 |
| $C_8$ Aromatics | 43.3 |
| Methylethylbenzenes | 0.50 |
| 1,3,5-Trimethylbenzene | 0.11 |
| 1,2,4-Trimethylbenzene | 27.8 |
| 1,2,3-Trimethylbenzene | 0.11 |
| Dimethylethylbenzenes | 4.50 |
| Diethylbenzenes | 0.0 |
| 1,2,3,5-Tetramethylbenzenes | 0.37 |
| 1,2,4,5-Tetramethylbenzenes | 16.8 |
| 1,2,3,4-Tetramethylbenzenes | 0.12 |
| Other | 0.71 |

These results show high selectivity to pseudocumene and durene, respectively, 99 percent and 97 percent.

EXAMPLES XI–XIII

Methanol and pseudocumene in equal mole ratio mixture were passed through the extruded catalyst from Example X with varying hydrogen to pseudocumene mole ratio at a wide range of reactor temperature. The conditions and results are reported below.

| EXAMPLE | XI | XII | XIII |
|---|---|---|---|
| Feed Composition, Mole Ratio | | | |
| Methanol/pseudocumene | 1 | 1 | 1 |
| H/HC | 9.6 | 9.1 | 8.0 |
| Reactor Conditions | | | |
| Temperature (°F.) | 610 | 720 | 820 |
| Pressure (psig) | 198 | 198 | 198 |
| WHSV (g liquid/hr) (g cat.) | 5.7 | 5.7 | 5.7 |
| Contact Time (Sec.) | 5.8 | 5.5 | 5.7 |
| Days on Stream | 1.2 | 1.4 | 1.6 |
| Liquid Product Composition (Wt. %) | | | |
| Paraffin and Naphthenes | 1.64 | 2.88 | 2.78 |
| Toluene | 0.12 | 0.26 | 0.49 |
| C$_8$ Aromatics | 1.27 | 3.33 | 4.94 |
| Methylethylbenzenes | 0.49 | 0.63 | 0.56 |
| 1,3,5-Trimethylbenzene | 0.13 | 0.79 | 4.13 |
| 1,2,4-Trimethylbenzene | 88.2 | 72.2 | 69.3 |
| 1,2,3-Trimethylbenzene | 0.09 | 0.40 | 1.82 |
| Dimethylethylbenzenes | 0.05 | 0.61 | 0.44 |
| Diethylbenzenes | 0.0 | 0.0 | 0.0 |
| 1,2,3,5-Tetramethylbenzenes | 0.16 | 1.11 | 3.55 |
| 1,2,4,5-Tetramethylbenzenes | 7.63 | 16.9 | 10.5 |
| 1,2,3,4-Tetramethylbenzenes | 0.16 | 0.46 | 1.26 |
| Other | 0.06 | 0.43 | 0.23 |
| Selectivity, Percent | | | |
| Durene in Total Tetramethylbenzenes | 96 | 91 | 69 |

These data show a high selectivity to durene is obtained in the methylation of pseudocumene over a wide range of reactor conditions.

What is claimed is:

1. A process for the selective production of pseudocumene and durene which comprises contacting a hydrocarbon feed comprising benzene or a methyl-substituted benzene under methylating conditions and in the presence of a methylating agent with a catalyst comprising AMS-1B crystalline borosilicate.

2. The process of claim 1, wherein the borosilicate is in hydrogen form.

3. The process of claim 1, wherein the methylating conditions comprise a temperature within the range of about 200° F. (93° C.) to about 1,100° F. (594° C.), a pressure within the range of about 0 psig (100 kPa) to about 2,000 psig (14,000 kPa), a WHSV with respect to hydrocarbon within the range of about 0.01 hr.$^{-1}$ to about 90 hr.$^{-1}$, a diluent gas-to-hydrocarbon mole ratio within the range of about 0.05 to about 20, a methylating agent-to-hydrocarbon mole ratio within the range of about 0.05 to about 20.

4. The process of claim 1, wherein the methylating agent is methanol, methyl chloride, methyl bromide, dimethylether or dimethylsulfide.

5. The process of claim 1, wherein said methylating agent is methanol.

6. The process of claim 3, wherein an ion or molecule of a Group IB, IIB, IIIB, IVB, VB, VIB, VIIB or VIII metal or a rare earth element is contained in the AMS-1B borosilicate-based composition as an additional catalytically active material.

7. The process of claim 6, wherein the additional catalytically active material is nickel.

8. The process of claim 3, wherein the catalyst comprising AMS-1B crystalline borosilicate and a porous refractory inorganic oxide, the borosilicate and the inorganic oxide having been intimately admixed with one another.

9. The process of claim 8, wherein at least one catalytically-active metal is placed onto the borosilicate prior to the borosilicate being mixed with the inorganic oxide.

10. A process for the selective production of pseudocumene or durene which comprises contacting toluene under methylating conditions and in the presence of a methylating agent with a catalyst comprising AMS-1B crystalline borosilicate.

11. The process of claim 10, wherein the methylating conditions comprise a temperature within the range of about 400° F. (204° C.) to about 950° F. (510° C.), a pressure within the range of 0 psig (100 kPa) to about 1,500 psig (10,000 kPa), a WHSV with respect to toluene within the range of about 0.1 hr.$^{-1}$ to about 20 hr.$^{-1}$, a diluent gas-to-toluene mole ratio within the range of about 0.1 to about 18, a methylating agent-to-hydrocarbon mole ratio within the range of about 0.1 to about 20.

12. The process of claim 11, wherein an ion or molecule of a Group IB, IIB, IIIB, IVB, VB, VIB, VIIB or VIII metal or a rare earth element is contained in the AS-1B borosilicate-based composition as an additional catalytically active material.

13. The process of claim 12, wherein in the additional catalytically active material is nickel.

14. The process of claim 11, wherein the borosilicate is in hydrogen form.

15. The process of claim 11, wherein the methylating agent is methanol.

16. A process for the selective production of pseudocumene or durene which comprises contacting xylenes under methylating conditions and in the present of a methylating agent with a catalyst comprising AMS-1B crystalline borosilicate.

17. The process of claim 16, wherein the methylating conditions comprise a temperature within the range of about 460° F. (237° C.) to about 950° F. (510° C.), a pressure within the range of about 0 psig (100 kPa) to about 1,500 psig (10,000 kPa), a WHSV with respect to C$_8$ aromatic hydrocarbon within the range of about 0.05 hr.$^{-1}$ to about 5 hr.$^{-1}$, a diluent gas-to-C$_8$ aromatic hydrocarbon mole ratio within the range of about 0.1 to about 18, a methylating agent-to-C$_8$ aromatic hydrocarbon mole ratio within the range of about 0.1 to about 20.

18. The process of claim 16, wherein the methylating agent is methanol.

19. A process for the selective production of durene which comprises contacting a feed comprising pseudocumene under methylating conditions and in the presence of a methylating agent with a catalyst comprising AMS-1B crystalline borosilicate.

20. The process of claim 19, wherein the methylating agent is methanol.

21. The process of claim 19, wherein said condition comprises a temperature within the range of about 460° F. (237° C.) to about 950° F. (510° C.), a pressure within the range of about 0 psig (100 kPa) to about 1500 psig (10,000 kPa), a WHSV with respect to pseudocumene within the range of about 0.05 hr.$^{-1}$ to about 50 hr.$^{-1}$ diluent gas-to-pseudocumene mole ratio within the range of about 0.1 to about 12 a methylating agent-to-pseudocumene mole ratio within the range of about 0.1 to about 20.

22. The process of claim 19, wherein molecule of a Group IB, IIB, IIIB, IVB, VB, VIB, VIIB or VIII metal or a rare earth element is contained in the AMS-1B borosilicate-based composition as an additional catalytically active material.

23. The process of claim 22, wherein the additional catalytically active material is nickel.

24. A process for producing at least one of pseudocumene and durene comprising reacting xylene and a methylating agent in the presence of a catalyst which is at least one crystalline borosilicate.

25. A process for the selective production of at least one of pseudocumene and durene comprising reacting a hydrocarbon feed comprising at least one of toluene or xylene with a methylating agent in the presence of a catalyst which is at least one crystalline borosilicate.

* * * * *